US005597953A

United States Patent [19]
Usanov et al.

[11] Patent Number: 5,597,953
[45] Date of Patent: Jan. 28, 1997

[54] GAS MOISTURE SENSOR AND METHOD OF PRODUCING SAME

[75] Inventors: Jury G. Usanov, ulitsa Elninskaya, 20, korpus 3, kv. 66; Jury A. Voronov; Pavel P. Polivanov, all of Moscow, Russian Federation

[73] Assignee: Jury Gennadievich Usanov, Moscow, Russian Federation

[21] Appl. No.: 454,241

[22] PCT Filed: Oct. 19, 1994

[86] PCT No.: PCT/RU94/00237

§ 371 Date: Jun. 12, 1995

§ 102(e) Date: Jun. 12, 1995

[87] PCT Pub. No.: WO95/11448

PCT Pub. Date: Apr. 27, 1995

[30] Foreign Application Priority Data

Oct. 19, 1993 [RU] Russian Federation ............ 93048472
Nov. 17, 1993 [RU] Russian Federation ............ 93051598

[51] Int. Cl.⁶ ..................................................... G01N 25/56
[52] U.S. Cl. ........................ 73/335.02; 73/25.04; 73/29.05
[58] Field of Search ............................. 73/29.02, 29.05, 73/335.02, 335.03, 335.05, 25.04

[56] References Cited

U.S. PATENT DOCUMENTS 4,203,087  5/1980  Kovac et al. ................... 73/335.02
4,793,181  12/1988  Djorup .......................... 73/335.02

FOREIGN PATENT DOCUMENTS 3437304  4/1986  Germany.
3806308  9/1989  Germany.
3829517  3/1990  Germany.
1651180  5/1991  U.S.S.R..
2126350  3/1984  United Kingdom.

OTHER PUBLICATIONS

"Otkrytia izobretenia", N 19, 1991, VNIIPI, (Moscow), S. 174, SU, A1, 1651180 (Nauchno–issledovatelsky institut . . . ) 23 May 1991 (23 May 1991) & an English translation thereof.

Primary Examiner—Michael Brock
Attorney, Agent, or Firm—Ladas & Parry

[57] ABSTRACT

A moisture sensor comprising a flat substrate, a moisture sensitive layer formed by spraying, and a tape heater formed by spraying. On a surface of the flat substrate made of monocrystalline silicon, a silicon dioxide film is formed by thermal oxidation, which functions as an insulation layer. The flat substrate is subjected to two-step etching. First, windows are etched in silicon dioxide film on both sides, opposite each other, a tape heater is deposited on one of the surfaces of the flat substrate and the unetched part of the silicon dioxide film. Windows are then etched in the other side of the flat substrate matched with the windows in the silicon dioxide film. A moisture-sensitive layer is further sprayed on the both sides of the tape heater located above the window in the flat substrate. The tape heater additionally functioning as a sensitive element with terminals.

7 Claims, 1 Drawing Sheet

GAS MOISTURE SENSOR AND METHOD OF PRODUCING SAME

TECHNICAL FIELD

This invention relates to measuring equipment and can be used for the measurement of gas and aerosol concentrations, in particular, water vapor in gas and aerosol mixtures as well as flow-velocity and temperature of aerosol and gas mixtures.

BACKGROUND OF THE INVENTION

Currently, known in the art is a moisture sensor (DE patent No. 3829517, cl. G01N25/56, 1989) wherein on a surface of a flat substrate made of low heat conductivity material, a tape heater in the form of meander is printed, on which an insulation layer is sprayed and on which, in turn, a moisture sensitive layer is deposited with a sensitive element inside the latter.

The prior art moisture sensor operates on the principle of cyclic conversion of a moisture sensitive layer parameter proportional to moisture of the environment, to an electric signal to be measured at the sensitive element outputs when the sensor reaches the ambient temperature. After the measurement period is finished, voltage is fed to the heater located on the substrate and separated from the moisture-sensitive layer by an insulating layer due to which a temperature of the whole moisture sensor begins to rise to the preset value, and as a result, the moisture-sensitive layer is dried; then the heating is stopped and the sensor cools down naturally, whereupon the measurement cycle is repeated.

Thus, the prior art moisture sensor has a long relaxation time (response speed), inasmuch as the heater and moisture sensitive layer are separated, which slows down a reaction of the moisture sensitive layer to ambient parameter changes.

Moreover, the prior art moisture sensor has a low efficiency due to the presence of an insulating layer between the heater and moisture sensitive layer, which leads to additional power consumption because power of the heater is additionally consumed for the heating of the insulating layer and substrate.

DISCLOSURE OF THE INVENTION

The object of the invention is to provide a moisture sensor of a new design which allows for a substantial increase in relaxation time (response speed) and efficiency.

Said object is achieved by a moisture sensor comprising a flat substrate, for example, rectangular, a moisture-sensitive layer formed by spraying, and a tape heater in a form of a broken line, for example, a meander, formed by spraying, wherein according to the present invention on a surface of said flat substrate, made of monocrystalline silicon, a silicon dioxide film, functioning as an insulation layer, is formed by thermal oxidation; windows, for example, rectangular, are etched in both faces of the silicon dioxide film, opposite each other; a tape heater is deposited on one of the faces of the flat substrate and the unetched part of the silicon dioxide film; a window, for example, rectangular, is etched in the other face of the flat substrate, said window being matched with the windows in the silicon dioxide film; a moisture-sensitive layer is further sprayed on both faces of the tape heater, located above the window in the flat substrate, said tape heater additionally functioning as a sensitive element with terminals.

The moisture sensor according to the present invention allows to reduce relaxation time (increase response speed) owing to the fact that the tape heater additionally functions as a sensitive element, i.e. an intermediate material separating the heating and sensitive elements is absent providing undelayed transmission information on environment parameters to the sensor output.

Additionally, this moisture sensor provides an efficiency improvement due to the fact that a contact between the substrate and tape heater is minimum, and there is no insulation layer between the heater and moisture sensitive layer.

BRIEF DESCRIPTION OF THE DRAWINGS

The invention is explained by a description of concrete embodiments of its construction with reference to the accompanying drawings, in which.

THE PREFERRED EMBODIMENT OF IMPLEMENTING THE INVENTION

Figure 2:
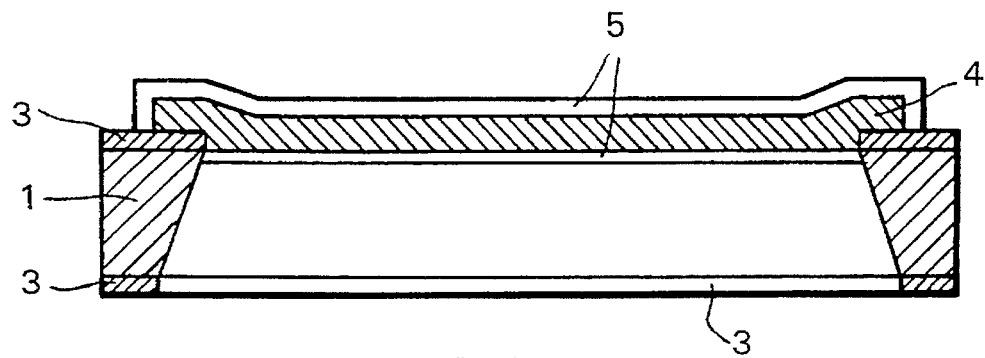
FIG. 2 shows a cross-section of the moisture sensor according to this invention.

A moisture sensor comprises a flat substrate 1, for example, rectangular, made of monocrystalline silicon, with a window 2; on a surface of the flat substrate 1 a silicon dioxide film 3 functioning as an insulation layer, is formed by thermal oxidation from a tape heater 4 made in the shape of broken line, for example, a meander, located above the window 2 in the flat substrate 1; both faces of said tape heater 4 are coated with a moisture-sensitive layer 5, terminals 6 of the tape heater 4 being the terminals of the moisture sensor. The tape heater 4 additionally functions as a sensitive element.

The moisture sensor of the invention operates as follows.

The moisture sensor operates on the principle of a cycle conversion of a moisture layer parameter proportional to the environment moisture, to an electric signal measured at the terminals 6 of the tape heater 4 in the process of heating the moisture sensor from ambient temperature to the preset one. When the measurement period is completed, the heating of the moisture sensor is stopped, and the moisture sensor cools down in a natural way. After cooling the measurement cycle is repeated.

To carry out the above described measurement process, the moisture sensor should be manufactured as follows.

Figure 1:
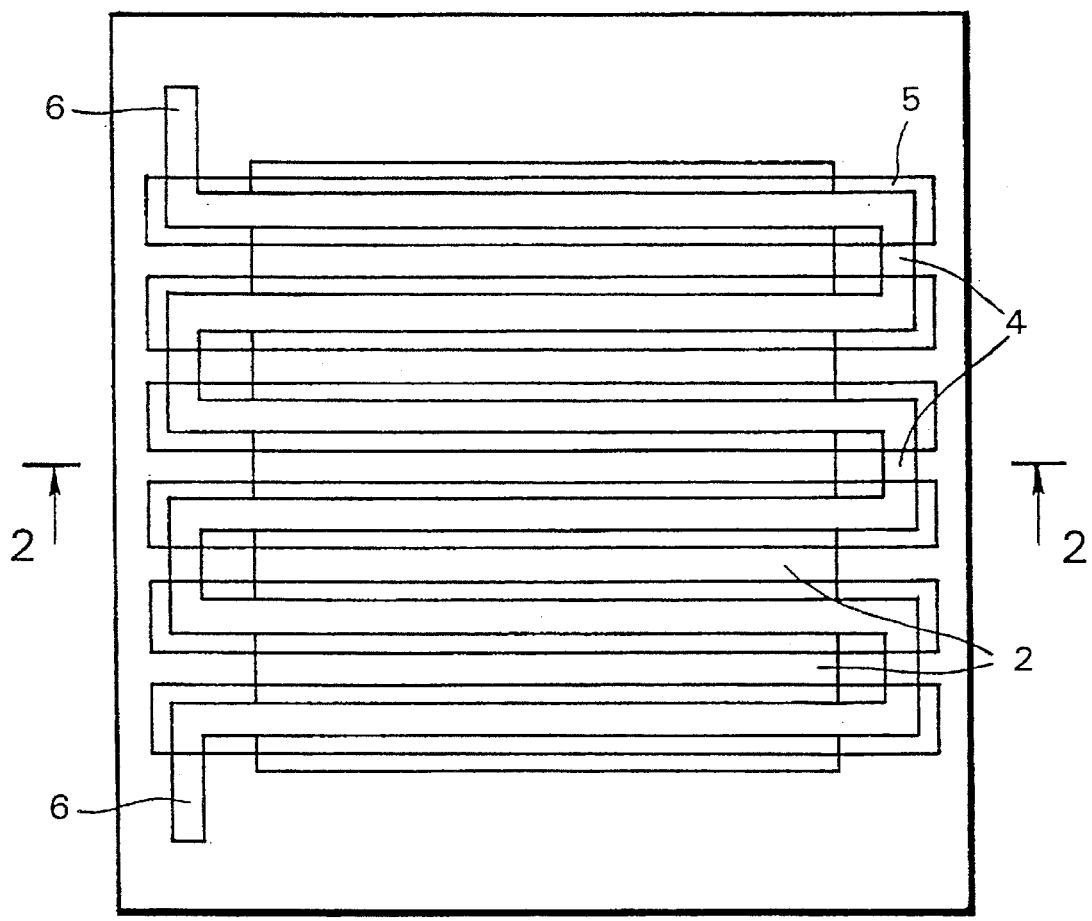
FIG. 1 shows a principal view of the moisture sensor according to the invention.

As a material for the flat substrate 1, monocrystalline silicon is used. To form an insulation layer, the flat substrate 1 is thermally oxidized with resulting silicon dioxide film 3. The flat substrate 1 is subjected to two-step etching. First, rectangular windows (not shown in FIG. 1) are etched in the silicon dioxide film 3 opposite each other, then tape heater 4 is thermally sprayed on one of the sides of the flat substrate 1 and unetched part of the silicon dioxide film. Further on, rectangular windows 2, matched with the windows in silicon dioxide film 3, are etched in the other side of the flat substrate 1 in monocrystalline silicon. After this a moisture sensitive layer 5 is sprayed on both faces of the tape heater 4. In some cases the operation of spraying the moisture sensitive layer 5 on the tape heater 4 can be modified. First, the moisture sensitive layer is applied to one side of tape heater 4 lying on the flat substrate 1 and the unetched part of the silicon dioxide film 3, and to the other side—after etching windows 2 in the flat substrate 1.

The moisture sensor starts a measurement cycle in the moment of supplying current to terminals 6 of the tape heater 4, resulting in heating of the moisture sensitive layer 5 and the environment. The time during which the tape heater 4 will be heated from the ambient temperature up to a certain (set) temperature will depend on the thermodynamic properties of the moisture-sensitive layer 5, and those of the environment near the moisture sensor. The time of heating the tape heater 4 will change with the environment moisture. After the tape heater 4 reaches a certain (set) temperature, the moisture-sensitive layer 5 is desorbed and the measurement cycle stops. Current is also cut off from the tape heater 4 and the process of cooling the moisture sensor begins during which the moisture sensitive layer 5 is saturated with moisture from the environment, and later on a new cycle of measurements is repeated.

Silicon dioxide film 3 separates the tape heater 4 from the flat substrate, i.e. it functions as an insulation.

However, when the substrate is made of a non-conductive material, there is no necessity to use the silicon dioxide film.

Thus, the moisture sensor according to the invention allows for reduction of relaxation time (increase response speed) due to the fact that the tape heater 4 additionally functions as a sensitive element, i.e. an intermediate material separating the heating and sensitive elements is absent, providing undelayed transmission of information on environment parameters to terminals 6 of the moisture sensor.

Moreover, this moisture sensor provides the efficiency improvement owing to the fact that a contact of the flat substrate 1 with the tape heater 4 is minimum, insofar as the tape heater 4 is connected to the substrate 1 not with all its surface, but only on the borders of the rectangular window 2 in the flat substrate 1 which stipulates the reduction of a heated area of substrate 1 and, accordingly, reduces power consumed.

Also, the efficiency is improved due to the absence of an insulation layer between the tape heater 4 and the moisture sensitive layer 5.

On the whole, the invented moisture sensor provides high accuracy, reliability and stability of operation.

Industrial Applicability

The present invention can be used in the manufacture of sensors of temperature, moisture, gas and aerosol concentration, flow velocity and pressure of gases and aerosols for respiratory medical equipment, infant incubators, artificial climate installations, etc.

We claim:

1. A moisture sensor comprising a flat substrate with silicon dioxide film thereon, windows etched in the silicon dioxide film on each side of the substrate, a tape heater deposited on one of the faces of the substrate and the unetched portion of the film, a window etched into the face of the substrate below the tape heater, said tape heater having two faces and a moisture sensitive layer on both faces of the tape heater.

2. The sensor as in claim 1 wherein the flat substrate is a monocrystalline silicon.

3. A gas moisture sensor comprising:

a flat substrate in the form of a frame and with a window, an insulation film disposed on sides of said flat substrate, a tape heater having a sensitive element consisting of a first group of sections, a second group of sections and two terminals, the tape heater disposed on said flat substrate so that said two terminals and said first group of sections of said sensitive element are disposed on said insulation film on one side of said substrate and coupled thereto, and said second group of sections of the sensitive element is disposed in said window, and a layer of moisture-sensitive material disposed on one side of said first group of sections of said tape heater and on both sides of said second group of sections of said tape heater.

4. A sensor as in claim 3 wherein monocrystalline silicon is used as the flat substrate.

5. A sensor as in claim 3 wherein silicon dioxide is used as the insulation film.

6. A sensor as in claim 3 wherein said tape heater is in the form of a meander.

7. A method of producing a gas moisture sensor comprising:

using a flat substrate of monocrystalline silicon, oxidizing a surface layer of the flat substrate to obtain an insulation film of silicon dioxide on the surface layer of said flat substrate, determining sections of identical size on opposite sides of said substrate, which are positioned symmetrically relative to each other and are designed for removal of said film of silicon dioxide therefrom, etching said film of silicon dioxide having said sections of identical size until all removal of silicon dioxide and attainment of two windows positioned symmetrically to each other on opposite sides of the flat substrate, forming a tape heater by disposing on one side of said flat substrate an electrically conducting material in the form of a tape having a first group of sections and terminals, the terminals being secured on said insulation film of silicon dioxide, and a second group of sections disposed in said etched window, applying an etcher from the other side of the flat substrate into said etched window in the silicon dioxide film and etching the monocrystalline silicon from the region located between said two windows in said silicon dioxide films to form a window in the flat substrate, applying a layer of moisture-sensitive material onto one side of said first group of sections of said tape heater, and applying a layer of moisture-sensitive material onto both sides of said second group of sections of said tape heater.

* * * * *